United States Patent [19]

Wu et al.

[11] 4,000,304
[45] Dec. 28, 1976

[54] DIURETIC ANTITUROMBOGENIC AND ANTIARRHYTHMIC PROCESSES USING N-SUBSTITUTED INDOLE DIMERS AND PYRROLOBENZODIA-ZEPINE REARRANGEMENT PRODUCTS THEREOF

[75] Inventors: Yao Hua Wu; Arthur Jacob Mueller, both of Evansville, Ind.

[73] Assignee: Mead Johnson & Company, Evansville, Ind.

[22] Filed: Mar. 24, 1975

[21] Appl. No.: 561,118

Related U.S. Application Data

[60] Division of Ser. No. 467,432, May 6, 1974, Pat. No. 3,895,031, which is a division of Ser. No. 251,059, May 8, 1972, Pat. No. 3,829,414, which is a division of Ser. No. 4,108, Jan. 19, 1970, Pat. No. 3,697,553, which is a continuation-in-part of Ser. No. 709,941, March 4, 1968, abandoned.

[52] U.S. Cl. .............................................. 424/274
[51] Int. Cl.$^2$ ........................................ A61K 31/40
[58] Field of Search .................................. 424/274

[56] References Cited

UNITED STATES PATENTS

| | | | |
|---|---|---|---|
| 3,637,748 | 1/1972 | Psaar et al. | 260/326.15 |
| 3,679,702 | 7/1972 | Wu et al. | 260/326.14 |

OTHER PUBLICATIONS

Ryan et al., Tetrahedron 12, pp. 2325–2337 (1971).
Wu et al., Jour. of Med. Chem. 15, pp. 529–534 (1972).
Amer et al., Research Communications in Chemical Pathology and Pharmacology 4, pp. 467–475 (1972).

*Primary Examiner*—Albert T. Meyers
*Assistant Examiner*—Daren M. Stephens
*Attorney, Agent, or Firm*—R. E. Carnahan; R. H. Uloth

[57] ABSTRACT

2-(2- or 3-Indolyl)indolines, unsubstituted and carbon substituted, condense with N-mono substituted carboxamides or with lactams under the influence of phosphorus oxychloride to produce 1-(N-substituted iminoalkyl)-2-(2- or 3-indolyl)indolines. The 2-(3-indolyl)-1-[2-(1-pyrrolinyl)]indolines rearrange to produce benzodiazepine derivatives. These products have diuretic, antituromobogenic, and antiarrhythmic activity on oral administration.

23 Claims, No Drawings

DIURETIC ANTITUROMBOGENIC AND ANTIARRHYTHMIC PROCESSES USING N-SUBSTITUTED INDOLE DIMERS AND PYRROLOBENZODIA-ZEPINE REARRANGEMENT PRODUCTS THEREOF

CROSS REFERENCE TO RELATED APPLICATIONS

This patent application is a divisional of co-pending U.S. patent application Ser. No. 467,432 filed May 6, 1974 now U.S. Pat. No. 3,895,031, patented July 15, 1975 which in turn is a divisional of U.S. patent application Ser. No. 251,059 filed May 8, 1972 and now U.S. Pat. No. 3,829,414 patented Aug. 13, 1974 which in turn is a divisional of U.S. patent application Ser. No. 4,108 filed Jan. 19, 1970 and now U.S. Pat. No. 3,697,553 patented Oct. 10, 1972 which in turn is a continuation-in-part of U.S. patent application Ser. No. 709,941 filed Mar. 4, 1968 and now abandoned.

FIELD OF THE INVENTION

Three related series of novel nitrogen heterocyclic compounds have been prepared by reaction of indole dimers with N-substituted carboxamides having a single carboxamide hydrogen atom. The invention involves the discovery that these substances have diruetic activity and includes processes for their synthesis and use as diuretic agents.

DESCRIPTION OF THE PRIOR ART

Indole and skatole and various other substituted indoles are known to dimerize under strongly acidic conditions to produce 2-(2- or 3-indolyl)indolines. Refer to B. Oddo, et al. Chem. Abstracts 19, 65 (1926); O. Schmittz-Dumont, Ann. 514, 267 (1934); O. Schmittz-Dumont, et al., Ber. 66, 766 (1933); H. F. Hodson, et al., J. Chem. Soc. 3544 (1951); and G. Berti, et al., Tetrahedron Letters No. 26, 13 (1960). These substances have been described in the literature largely as a result of basic studies on the chemistry of indole. They have not heretofore been found to be of utility in the field of medicinal chemistry.

The thiazide diuretics typified by 6-chloro-7-sulfamoyl-1,2,4-benzothiadiazine-1,-dioxide (chlorothiazide) have largely replaced the organo mercurial compounds which were introduced as diuretics nearly 50 years ago. Both are unrelated chemically to the substances of this invention. More recently other types of organic compounds have been reported as diuretic agents. They include 4-chloro-N-furfuryl-5-sulfamoylanthranilic acid (furosemide), 2,4,7-triamino-6-phenylpteridine (triamterene) and certain steroid compounds which are aldosterone antagonists. Each of these also belongs to a different chemical class than the substances of the present invention.

SUMMARY OF THE INVENTION

The novel substances of the present invention have the following formulas.

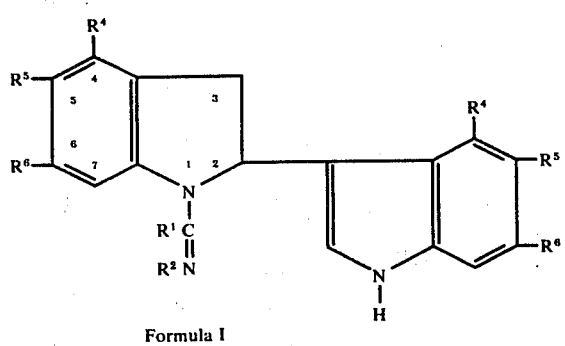

Formula I

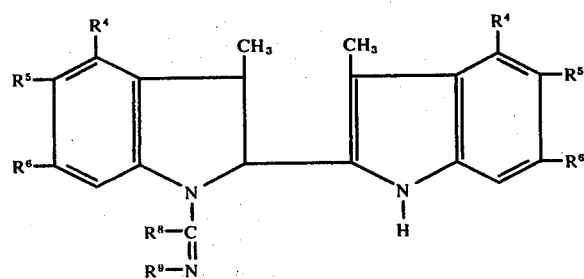

Formula II

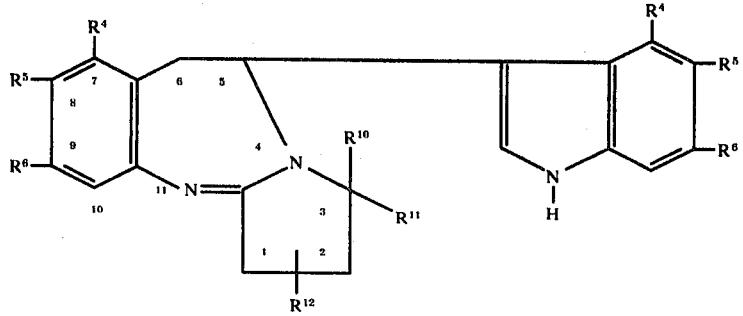

Formula III

The ring positions are numbered in Formulas I and III for nomenclature purposes. The position numbers for Formula II are the same as for Formula I.

In Formulas I, II, and III $R^4$, $R^5$, and $R^6$ maybe hydrogen, halogen, alkyl having 1 to 4 carbon atoms, alkoxy having 1 to 12 carbon atoms, aralkoxy having 7 to 12 carbon atoms, alkanoyl having 2 to 4 carbon atoms, nitro, or cyano.

In Formula I, $R^1$ is hydrogen or alkyl having 1 to 4 carbon atoms and $R^2$ is alkyl having 1 to 8 carbon atoms, or cycloalkyl or polycycloalkyl having 3 to 10 carbon atoms. $R^1$ and $R^2$ may be joined to form a 2-(1-pyrrolinyl) group which may be carbon substituted by up to 3 alkyl groups each having from 1 to 4 carbon atoms.

In Formula II, $R^8$ is hydrogen or alkyl having 1 to 4 carbon atoms. $R^9$ is alkyl having from 1 to 8 carbon atoms or cycloalkyl or polycycloalkyl having 3 to 10 carbon atoms. $R^8$ and $R^9$ may be joined to form a heterocyclic function having a 5, 6, or 7 membered ring which in turn may be carbon substituted by up to 3 alkyl groups having from 1 to 4 carbon atoms.

In Formula III, $R^{10}$, $R^{11}$, and $R^{12}$ may be hydrogen atoms or lower alkyl groups having from 1 to 4 carbon atoms. $R^{12}$ is located in either the 1- or 2-positions.

The term polycycloalkyl is intended to refer to an alicyclic substituent having up to 10 carbon atoms and more than one ring such as adamantyl.

The present invention also includes the acid addition salts of the compounds of Formulas I, II, and III. Pharmaceutically acceptable acid addition salts are, of course, selected when the product is to be used as a medicinal agent. For synthesis and purification purposes, however, salts of acids which are not pharmaceutically acceptable are sometimes useful. For example, for resolution studies, acids such as d-camphorsulfonic acid or other optically active acid may be selected for preparation of diasteroisomeric salts according to conventional resolution methods. In other instances salts with acids which are not pharmaceutically acceptable may be found useful as intermediates in synthesis of the pharmaceutical end products for instances when they have desirable crystallization properties.

The pharmaceutically acceptable acid addition salts are those in which the anion does not contribute significant toxicity to the salt in the dosages employed in accordance with the present invention. Examples of suitable salts are the acetate, propionate, butyrate, pamoate, tannate, mucate, citrate, maleate, tosylate, mesylate, phosphate, nitrate, sulfate, hydrobromide, hydroiodide, hydrochloride, etc. salts.

The compounds of the present invention have one, two, or more asymmetric carbon atoms and consequently, exist in a number of stereoisomeric forms. Those of Formula I have an asymmetric carbon atom in the 2-position of the indoline ring. Those of Formula II have asymmetric carbon atoms at both the 2- and 3-positions of the indoline ring. Those of Formula III have an asymmetric carbon atom in the 5-position. $R^1$, $R^2$, $R^4$, $R^5$, $R^6$, $R^8$, $R^9$, $R^{10}$, $R^{11}$, and $R^{12}$ and the pyrrolidine ring of Formula III may contain additional asymmetric centers. Purified racemic modifications and optical isomers of a given individual structural type have diuretic potencies not substantially different from other stereoisomeric forms of the same structural type. Accordingly, it is intended to include each of the stereoisomeric forms of the structures referred to herein within the present invention. In some instances, one or the other of the various stereoisomers may be preferred for pharmaceutical purposes by virtue of other properties which are unique.

DETAILED DESCRIPTION OF THE INVENTION

CHEMICAL SYNTHESIS

The compounds of Formulas I and II are prepared by reaction of an indole dimer of Formula IV or a skatole dimer of Formula V respectively with a carboxamide as is illustrated in the following equations. The substances of Formula III are prepared by rearrangement from certain Formula I compounds. The substituents $R^1$, $R^2$, $R^4$, $R^5$, $R^6$, $R^8$, and $R^9$ have the same meanings as previously defined.

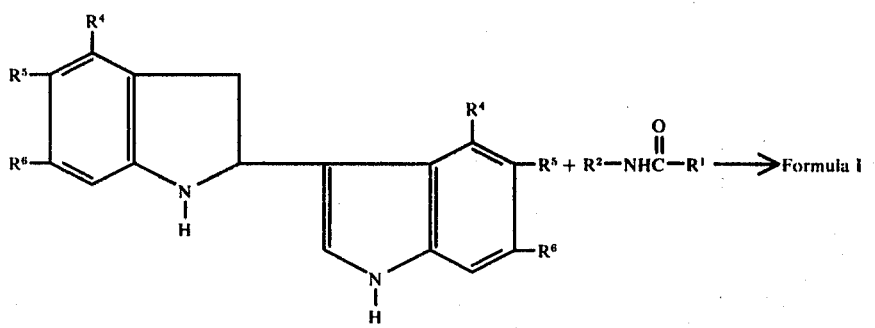

Formula IV

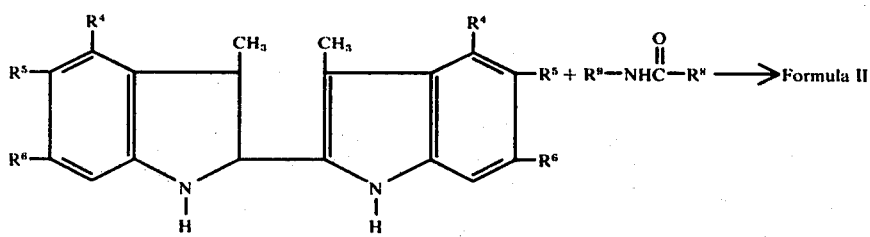

Formula V

From 1 to 2 molecular proportions of the carboxamide and one molecular proportion of the indole or skatole dimer are dissolved or suspended in an inert solvent and treated with substantially one molecular proportion of phosphorus oxychloride. The aprotic, water immiscible solvents including the liquid hydrocarbons, chlorinated hydrocarbons and ethers, including 1,2-dichloroethane, chloroform, carbon tetrachloride, diethyl ether, di-(n-butyl) ether, benzene, hexane, etc. are preferred. The mode of addition is not critical, that is, a solution or suspension of the indole dimer and carboxamide may be added to a solution of the phosphorus oxychloride, or a solution of the phosphorus oxychloride in the solvent may be added to a solution of the other reactants. The reaction takes place in a facile manner and it does not require prolonged periods for completion. Reaction temperatures in the range of about −20° C. up to about 40° C. are operable. The process is exothermic and, accordingly, external cooling is generally necessary to maintain the reaction mixture within the foregoing temperature range. For convenience and economy temperatures approximating room temperature are preferred. Efficient stirring is desirable. Reaction times of the order of from about 1 to 15 hrs. are employed.

The product is recovered by pouring the reaction mixture into an aqueous solution of a base, or into water to hydrolyze the reaction complex. The product is extracted into the organic solvent layer. It is preferred to employ water immiscible solvents to facilitate isolation of the reaction product. The product is then recovered from the solvent extract by evaporation and crystallization. Acid addition salts are prepared in conventional fashion by treatment of the free base form of the product, preferably in solution, with the desired acid. Organic solvents such as ethanol and ether are preferred for the preparation of the acid addition salts since they crystallize from these solvents.

The indole or skatole dimer starting materials may be prepared in situ and used without isolation if desired employing the corresponding indole or skatole as raw material. This mode of operation, however, generally affords lower yields and is not preferred. Reaction yields according to the preferred method are generally of the order of 50% or greater.

With respect to preparation of the substances of Formula I wherein $R^1$ and $R^2$ are joined to form the 2-pyrrolinyl group (as shown in Formula VI) which may be substituted by from 1 to 3 alkyl groups, certain precautions are desirable in application of the foregoing method due to the fact that these substances when in the free base form are subject to rearrangement into the 2,3,5,6-tetrahydro-5-(indol-3-yl)-1H-pyrrolo[2,1-b][1,3]benzodiazepines of Formula III. This is illustrated by the following equation.

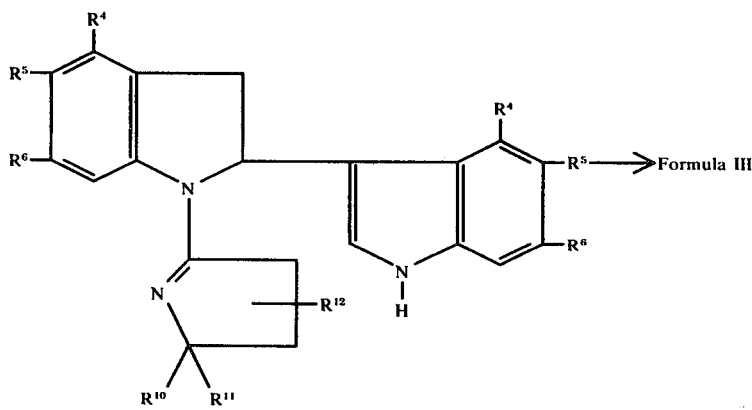

Formula VI

In Formula VI, $R^4$, $R^5$, $R^6$, $R^{10}$, $R^{11}$, and $R^{12}$ have the same meaning as previously stated. The propensity for the substances of Formula VI to undergo the rearrangement is inversely related to the number of alkyl groups in the pyrrolinyl ring, $R^{10}$, $R^{11}$, and $R^{12}$. In those instances where each of $R^{10}$, $R^{11}$, and $R^{12}$ are hydrogen atoms or only one of them is alkyl, rearrangement to the benzodiazepine structure, Formula III, occurs on warming the free base Formula VI in ethanol. Thus, attempts to recrystallize the substances of Formula VI frequently leads to rearrangement. When $R^{10}$ and $R^{11}$ are each alkyl groups in the substance of Formula VI, heating for prolonged periods of the order of 60 hrs. in refluxing butanol is necessary to effect rearrangement.

The rearrangement is facilitated by polar solvents and particularly the protic solvents including the lower alkanols. In some instances the rearrangement takes place thermally. For example, when $R^{10}$, $R^{11}$, and $R^{12}$ are hydrogen atoms heating at 180° C. in the absence of a solvent brings about the rearrangement. On the other hand, when $R^{10}$ and $R^{11}$ are methyl groups and $R^{12}$ is a hydrogen atom the substance is thermally stable up to 300° C.

As a general statement the preferred method for the preparation of the benzodiazepine of Formula III involves heating a solution of the indolylindoline of Formula VI in a protic solvent for a period of from about 1 to 60 hrs. at a temperature of from about 65° to 150° C. and preferably from about 80° to 120° C. Preferred solvents are the alkanols and polyols having up to about 6 carbon atoms. Conversely in preparing an indolylindoline of Formula VI, the foregoing conditions should be avoided. None of the substances of Formula II nor those of Formula I in which $R^1$ is hydrogen or alkyl and $R^2$ is alkyl, cycloalkyl, or polycycloalkyl are subject to the rearrangement described for the compounds of Formula VI.

The substances of Formula III are novel compounds which have been fully characterized as to structure and properties. Generally speaking they are less soluble and thus somewhat less tractable for pharmaceutical purposes than their counterparts of Formula I. This reduced solubility facilitates their separation from synthesis mixtures resulting from the rearrangement procedure, and their purification by crystallization. They are active diuretic agents and are therefore considered part of the present invention. They form acid addition salts and exist in various stereoisomeric forms just as do the substances of Formula I.

PHARMACOLOGY

The compounds of Formulas I, II and III are diuretic agents which are orally effective in mammals and characterized by high potency with reference to the thiazides and mercurial diuretics. The presence of an effective amount of many of these substances in the mammalian circulatory system has the added benefit of affording a protective antithrombogenic and cardiac antiarrhythmic effect.

Urine flow, sodium excretion and chloride excretion are increased following oral or parenteral administration of the substances of Formulas I, II and III; bicarbonate excretion is unchanged. With preferred members of the series, potassium excretion is unchanged or reduced. The disadvantages associated with prior widely used diuretics are believed to stem largely from a lack of one or more of the foregoing characteristics. For example, the thiazides cause an increased excretion of potassium. The mercurials must be administered by injection. Other agents which do not suffer from those disadvantages lack the potency of the present substances.

The diuretic properties have been examined for a large number of the compounds of Formulas I, II and III in studies in rats. Detailed studies in dogs have confirmed the rat findings, and have shown that the diuretic effects are the result of a different mechanism of action from that of currently popular diuretics such as hydrochlorthiazide, triamterene, and mercaptomerin (a mercurial). Use of the substances of Formulas I, II and III in combination with other diuretics and, more particularly, their applicability in instances where lack of response to other diuretics is encountered is therefore suggested.

The substances of Formulas I, II and III exert their optimum effects when administered to mammals in non-toxic doses ranging from about 0.1 to 25 mg./kg. of body weight per day. In mice, doses in the range of from 25 to 1000 mg./kg. of body weight administered orally are without any undesired effects whatsoever, and the lethal doses ($ALD_{50}$) for mice treated orally are from 2 to 10 or more times larger. $ALD_{50}$ values for mice treated orally are in the range of 50 to 2000 mg./kg. The substances may be administered orally or parenterally but the oral route is preferred and is nearly always applicable due to the prompt onset of action of the present compounds.

Evaluation of the diuretic action may be made by the method of Lipschitz, et al. (Jour. Pharma. & Experi. Thera. 79, 97 (1943)). According to this method, fasted rats are hydrated orally with 25 mg./kg. of body weight of isotonic saline solution after arranging them into groups of 8 for dosing. The saline solution serves as the vehicle for dosing. One control group receives a dose of 960 mg./kg. of body weight of urea, and the effects of the medications used in the other groups are related to it. The animals of two further groups receive doses, preferably at different levels, of a standard reference diuretic agent such as hydrochlorthiazide. The animals of all remaining groups are treated with various doses of the test substance. Immediately after treatment, the animals are placed in metabolism cages (two rats of the same group per cage) and left without food or water for five hours. The volume of urine excreted by each pair is determined after this period and the urines are analyzed for sodium, potassium, and chloride. The results for the test drugs are expressed as ratios of the volume of urine or total quantities of electrolytes excreted during the experimental period to the values observed for the urea control group.

The compounds of Formulas I, II and III were administered in oral doses in the foregoing test over the range of 3.1 to 50.0 mg./kg. of body weight. The maximum diuresis achieved with hydrochlorthiazide which was tested for comparison occurred at a dose of 12.5 mg./kg. of body weight, and was approximately 1.5 fold that of urea. With few exceptions the substances of Formulas I, II and III described in the following examples substantially exceeded this degree of activity. In general, at the maximally effective dose of each, the amount of potassium excreted was less than that excreted by the hydrochlorthiazide controls and in many instances less than that excreted by the urea controls.

In the dog almost instantaneous diuresis occurred on intravenous injection of 2 mg./kg. of 2,3,5,6-tetrahydro-5-(indol-3-yl)-1H-pyrrolo[2,1-b][1,3]benzodiazepine. Continuous intravenous infusion at the rate of 2 mg./kg. per hour thereafter afforded maximal diuretic effect.

The antithrombogenic activity of the substances of Formulas I, II and III is evident on evaluation thereof according to the method of Born, Nature 194, 927 (1962) or O'Brien, J. Clin. Path. 15, 446 (1962). This is a nephelometric method in which the change in turbidity of a specimen of platelet rich blood plasma is measured on causation of platelet aggregation by addition of a thrombogenic agent such as adenosine diphosphate, epinephrine, serotonin, or a long-chain saturated fatty acid. In the evaluation of the present substances adenosine diphosphate is an appropriate thrombogenic agent. An increase in transmittance of light occurs when the thrombogenic agent is added to the specimen of platelet rich plasma due to clumping of the platelets. Efficacy of a test compound is determined by its ability to prevent this clumping and concomitant increase in transmittance. With active compounds various concentrations are tested and that concentration causing a 50% reduction in the thrombogenic response is determined from a concentration-response curve. The resulting figures are convenient for comparing the activity of various compounds. Significant activity was exhibited in this test with the products of Examples 1, 3, 7, 9, 11-19, 22, 25, 28, 29, 36, and 39. These substances at concentrations of the order of 50 mcg./ml. reduced the thrombogenic capacity of adenosine diphosphate, 2 mcg./ml. by 50% or more.

Antiarrhythmic activity is evaluated in mice weighing 18 to 25 g. treated intraperitoneally with the test compound according to the method of Lawson, J. Pharmacol. Exp. Therap. 160, 22, (1968). According to this test cardiac arrhythmia is induced by causing the mouse to inhale chloroform until respiratory arrest occurs. The ability of a test compound to forestall the concomitant cardiac arrhythmia is measured by pretreatment of the animals with the substance by intraperitoneal injection and observation of the heart for arrhythmia visually through an incision made after respiratory arrest occurs. The substances of Examples 17, 28, 29, and 30 exhibited anti-arrhythmic capacity comparable to that of quinidine sulfate. Anti-arrhythmic activity is also demonstrable in the test for the products of Examples 7, 12, 14, 15, 18, 19, 21, 25, 31, 33, 34, and 37.

DESCRIPTION OF THE PREFERRED EMBODIMENTS

EXAMPLE 1.

2-(3-Indolyl)-1-[2-(1-pyrrolinyl)]indoline hydrochloride.

A mixture of 23.43 g (0.1 mole) of 2-(3-indolyl)indoline and 17.02 g. (0.2 mole) of 2-pyrrolidone in 150 ml. of 1,2-dichloroethane is treated with a solution of 15.33 g. (0.1 mole) of phosphorus oxychloride in 50 ml. of 1,2-dichloroethane in one lot. The reaction temperature rises to 54° C. and then cools to 30° C. during a period of about 1¼ hrs. The mixture is then cooled to ice temperature in an ice bath and treated with 80 ml. of ice water. The organic solvent layer is drawn off and the aqueous layer containing some suspended solid is extracted with 50 ml. of dichloroethane. The combined dichloroethane solutions are then dried over anhydrous sodium sulfate and the solvent removed by distillation yielding a solid residue weighing 18 g. (31%). This is the crude hydrochloride salt of the desired product. It is purified by recrystallization from a mixture of 15 ml. of methanol and 50 ml. of isopropanol; yield 6.92 g.

The aqueous portion of the reaction mixture is then treated with 80 ml. of concentrated ammonium hydroxide (29% and the mixture extracted with 150 ml. of dichloroethane. The dichloroethane extract is dried, and concentrated to one sixth of its original volume and diluted with 150 ml. of low-boiling petroleum ether to yeild 16.6 g. of a low-melting solid which is a crude form of the desired product in free-base form. For further purification, this material is converted to the hydrochloride salt by treatment thereof in 170 ml. of ethanol with hydrogen chloride. The hydrochloride precipitates from the ethanolic solution after treatment with 200 ml. of ether; yield 15.9 g. (27.5%). A portion of the combined hydrochloride salts, weighing 22.8 g. is refluxed with 540 ml. of ethanol to effect solution, allowing the solution to cool, and collecting the crystalline product which separates, yield 12.4 g., m.p. 213.5°–215.5° C. Further quantities of the product may be recovered by concentration of the filtrate.

Anal. Calcd. for $C_{20}H_{19}N_3.HCl$: C, 71.09; H, 5.97; Cl, 10.50; N, 12.44. Found: C, 71.05; H, 6.02; Cl, 10.49; N, 12.30.

EXAMPLE 2.
2-(3-Indolyl)-1-[2-(1-pyrrolinyl)]indoline.

A sample of the product of Example 1, 0.9 g., is converted to the free base form by suspending it in 100 ml. of water and adjusting the solution to an alkaline pH with 40% aqueous sodium hydroxide. The base precipitates and is collected on a filter. It is recrystallized from isopropyl ether, m.p. 159°–161° C.

Anal. Calcd. for $C_{20}H_{19}N_3$: C, 79.70; H, 6.36; N, 13.94. Found: C, 79.56; H, 6.83; N, 13.82.

Ultraviolet absorption maxima (methanol); 289 mµ ($\epsilon$ 11,740), 265 mµ ($\epsilon$ 17,850).

Infrared absorption maxima (5% in potassium bromide) occur at: 6.20, 6.31, 6.74, 6.86, 7.05, 8.14, 8.60, 9.02, 9.49, 9.89, and 13.42µ.

The nuclear magnetic spectrum measured on a 10% solution of this compound in deuterochloroform with tetramethylsilane as reference has the following characteristics.

Table 1.

| Chemical Shift, δ (ppm) | Relative Area | Multiplicity | J (cps) | Structural Feature |
|---|---|---|---|---|
| 8.20 | 1 | doublet of doublets | | 1 |
| 5.71 | 1 | doublet of doublets | 3.0, 9.5 | 2 |
| 3.08 | 1 | doublet of doublets | 3.0, 16.0 | 3 |
| 3.70 | 1 | doublet of doublets | 9.5, 16.0 | 4 |
| 8.70 | 1 | broad singlet | | 5 |
| 2.65 | 2 | multiplet | | 6 |
| 1.87 | 2 | multiplet | | 7 |
| 3.81 | 2 | triplet | | 8 |

EXAMPLE 3.
2,3,5,6-Tetrahydro-5-(indol-3-yl)-1H-pyrrolo-[2,1-b][1,3]benzodiazepine.

The same reactants are employed as in Example 1. They are mixed in the same way and then cooled to ice temperature after a reaction period of about 1 hr. The mixture is then poured into 300 ml. of concentrated aqueous ammonium hydroxide (29%) containing 100 g. of crushed ice with stirring. The clear aqueous layer is separated, washed once with 100 ml. of 1,2-dichloroethane and the combined 1,2-dichloroethane solutions containing the product dried over anhydrous magnesium sulphate. The solution is concentrated to a thick residue which is dissolved in 150 ml. of 80% ethanol. This solution is concentrated by boiling on a steam bath for about 1 hr. and allowing the solvent to evaporate until crystallization commences. It is at this stage that rearrangement of the substance described in Example 1 to the pyrrolobenzodiazepine structure occurs. The product weighing 13.4 g. (45%) is collected after crystallization is complete, m.p. 234°–238° C.; after recrystallization from absolute ethanol, m.p. 234°–236° C.

Anal. Calcd. for $C_{20}H_{19}N_3$: C, 79.70; H, 6.36; N, 13.94. Found: C, 79.80; H, 6.67; N, 13.95.

Infrared absorption maxima (5% in potassium bromide) occur at: 6.30, 6.41, 6.85, 7.0, 7.14, 7.40, 7.71, 7.87, 8.26, 8.83, 9.17, 13.06, and 13.52µ.

The nuclear magnetic resonance spectrum measured as a 10% (weight/volume) solution in trifluoroacetic acid with 2% tetramethylsilane added as an internal reference revealed the following chemical shifts ($\tau$ or $\delta$) and coupling constants (J).

Table 2.

| Chemical Shift | | Relative Area | Multiplicity | Structural Feature |
|---|---|---|---|---|
| τ | δ(ppm) | | | |
| 0.52 | 9.48 | 1 | Broad Singlet | NH |
| 2.29 | 7.71 | 1 | Doublet of doublets | Aromatic ring protons |
| 2.9 | 7.1 | 7 | Multiplet | |
| 3.32 | 6.68 | 1 | Sharp singlet | —CH═[2] |
| 4.37 | 5.63 | 1 | Triplet J=4.0 cps | —CH—[1] |
| 5.93 | 4.07 | 2 | Triplet J=7.2 cps | —CH$_2$—[3] |
| 6.37 | 3.63 | 2 | Doublet J=4.0 cps | —CH$_2$—[4] |
| 6.52 | 3.48 | 2 | Triplet J=8.3 cps | —CH$_2$—[5] |
| 7.66 | 2.34 | 2 | Multiplet | —CH$_2$—[6] |

[1] 5-position of the pyrrolobenzodiazepine ring
[2] 2-position of the indole ring
[3] 3-position of the pyrrolobenzodiazepine ring
[4] 6-position of the pyrrolobenzodiazepine ring
[5] 1-position of the pyrrolobenzodiazepine ring
[6] 2-position of the pyrrolobenzodiazepine ring

Table 2.-continued

NMR Characteristics Example 3

| Chemical Shift τ | δ(ppm) | Relative Area | Multiplicity | Structural Feature |
|---|---|---|---|---|

[Structure diagram of a pyrrolobenzodiazepine compound with indole substituent, showing numbered positions 1-6]

The nuclear magnetic resonance spectra of the products of Examples 2 and 3 illustrate certain key features which are typical of the substances of this invention and which are useful in distinguishing an indolylindoline of Formula I (Examples 2 and Table 1) from the corresponding pyrrolobenzodiazepine of Formula III (Example 3 and Table 2). Referring to Table 1, the chemical shift at 8.20 ppm comprised of a doublet of doublets is a consequence of the deshielding effect of the pyrroline group on the aromatic proton in the 7-position. This down field shift of one of the aromatic proton signals is characteristic of the indolylindolines of Formula I. The H-7 chemical shift is evident in the nmr spectra of each of the substances of Formula I and is in the range of 7.6 to 8.2 ppm. The nmr spectra of the acid addition salts do not reflect the H-7 down field shift.

A second key point is the doublet of doublets appearing at 5.71 ppm in the spectrum of Example 2 (Table 1). The spacing of these peaks is such that one doublet exhibits a high coupling constant; usually near 10 cps, and the other a low coupling constant. This is the result of the stereochemical relationship between the hydrogen atoms in the 2- and 3-positions of the indoline ring, one of those in the 3-position being nearly eclipsed with that in the 2-position resulting in a high coupling constant. The corresponding chemical shift in the pyrrolobenzodiazepines appears as a doublet of doublets with nearly equivalent coupling constants in some instances appearing as a triplet. This is due to the fact that more nearly equivalent interaction between the C-5 and C-6 hydrogen atoms is possible in the benzodiazepine. This feature is reported as a triplet at 5.63 ppm (J=4.0 cps) in the spectrum of Example 3 (Table 2).

EXAMPLE 4.

2,3,5,6-Tetrahydro-5-(indol-3-yl)-1H-pyrrolo[2,1-b][1,3]benzodiazepine hydrochloride.

A portion of the product of Example 3, 12 g., is suspended in 150 ml. of absolute ethanol and treated with one chemical equivalent of 5.02 N ethanolic hydrogen chloride. A clear solution results which is diluted with 200 ml. of anhydrous ether resulting in precipitation of the desired hydrochloride salt. The salt is collected on a filter and recrystallized from a mixture of 150 ml. of ethanol and 150 ml. of ether, yielding 9.3 g. (69.1%) of pure product, m.p. 262°–264° C.

Anal. Calcd. for $C_{20}H_{19}N_3 \cdot HCl$: C, 71.09; H, 5.97; Cl, 10.50; N, 12.44. Found: C, 71.38; H, 5.90; Cl, 10.26; N, 12.65.

A mineral oil suspension of the substance exhibits the following absorption maxima in the infrared: 6.04 (characteristic of the amidinium group at the 4–11 position of the ring), 6.21, 6.30, 7.74, 8.14, 8.68, 9.04, 9.67, 12.86, 13.01, 13.31, and 13.41μ. In the ultraviolet a single peak is exhibited: $\lambda_{max.}^{H_2O}$ 259 mμ (ε = 16,270).

EXAMPLE 5.

2,3,5,6-Tetrahydro-5-(indol-3-yl)-3-methyl-1H-pyrrolo[2,1-b][1,3]benzodiazepine.

The procedure of Example 3 is repeated substituting 0.2 moles of 5-methyl-2-pyrrolidone for the 2-pyrrolidone specified in Example 3. The product is recovered in the fashion described there and recrystallized from 80% aqueous ethanol, m.p. 190°–192° C.

Anal. Calcd. for $C_{21}H_{21}N_3$: C, 79.97; H, 6.71; N, 13.32. Found: C, 79.80; H, 6.87; N, 12.93.

The nuclear magnetic resonance spectrum of this substance measured in deuterodimethylsulfoxide with tetramethylsilane as reference exhibits the following characteristics.

Table 3.

NMR Characteristics Example 5

| Chemical Shift | Relative Area | Multiplicity | Structural Feature |
|---|---|---|---|
| 7.69 | 1 | doublet of doublets | H-10 |
| 10.67 | 1 | broad singlet | NH |
| 5.32 | 1 | doublet of doublets (J=3.5 and 5.5 cps) | H-5 |
| 3.25 | 2 | multiplet | H-6 |
| 1.23 | 3 | doublet (J=6.2 cps) | $CH_3$-3 |
| 3.60 | 1 | multiplet | H-3 |
| 2.05 | 2 | multiplet | H-2 |
| 2.63 | 2 | multiplet | H-1 |

EXAMPLE 6.

2,3,5,6-Tetrahydro-5-(indol-3-yl)-3-methyl-1H-pyrrolo[2,1-b][1,3]benzodiazepine hydrochloride.

The product of Example 5 is converted to the hydrochloride salt as described in Example 4; recrystallized from ethanol, m.p. 243.5°–245.5° C.

Anal. Calcd. for $C_{21}H_{21}N_3 \cdot HCl$: C, 71.68; H, 6.30; N, 11.94. Found: C, 71.92; H, 6.33; N, 12.17.

EXAMPLE 7.

2-(3-Indolyl)-1-[2-(5-methyl-1-pyrrolinyl)]-indoline hydrochloride.

The procedure of Example 1 is repeated substituting 0.2 moles of 5-methyl-2-pyrrolidone for the 2-pyrrolidone specified in Example 1. In this instance after the reaction period and cooling of the reaction mixture it is poured into 200 ml. of cold concentrated ammonium hydroxide (29%) then stirred for 10 minutes before separation of the organic solvent layer. The solvent layer is dried over magnesium sulfate and then chilled in an ice bath resulting in crystallization of 10.0 g. of the desired product as the free base, m.p. 173°–178° C. This material is immediately converted to its hydrochloride salt by dissolving in 100 ml. of ethanol and treating with hydrogen chloride. Approximately, 250 ml. ether is mixed with the resulting solution resulting in crystallization of 9.6 g. of the hydrochloride salt. This material is recrystallized from a mixture of 75 ml. of ethanol and 200 ml. of ether, yield 8.3 g. (23.6%), m.p. 194.5°–199.5° C., dec.

Anal. Calcd. for $C_{21}H_{21}N_3 \cdot HCl$: C, 71.68; H, 6.30; N, 11.94; Cl, 10.08. Found: C, 71.69; H, 6.31; N, 11.64; Cl, 9.78.

Nuclear magnetic resonance spectrum of this hydrochloride salt using trifluoroacetic acid as solvent revealed the following characteristics.

Table 4.

| Chemical Shift δ(ppm) | Relative Area | NMR Characteristics Example 7 Structural Feature | Multiplicity |
|---|---|---|---|
| 7.68 | 1 | indoline H-7 | multiplet |
| 5.65 | 1 | indoline H-2 | multiplet |
| 3.5 | 4 | pyrroline H-2 indoline H-3 | broad singlet |
| 2.24 | 2 | pyrroline H-4 | multiplet |
| 4.24 | 1 | pyrroline H-5 | multiplet |
| 1.53) | 3 | pyrroline $CH_3$-5 | (doublet |
| 1.47) | | | (doublet |

The twin doublets for the pyrroline $CH_3$-5 together integrating for three protons at 1.53 ppm and 1.47 ppm indicate that the sample is a mixture of the two possible racemic mixtures. The multiplet at 5.65 ppm for the indoline H-2 rather than the normal doublet of doublets is further evidence for the presence of both racemates.

EXAMPLE 8.

2-(3-Indolyl)-1-[2-(5-methyl-1-pyrrolinyl)]-indoline.

The product of Example 7 is converted to the free base according to the method of Example 2. It is recrystallized from 1,2-dichloroethane, m.p. 176°–178° C.

Anal. Calcd. for $C_{21}H_{21}N_3$: C, 79.97; H, 6.71; N, 13.32. Found: C, 79.72; H, 6.69; N, 13.14.

The nuclear magnetic resonance spectrum run in deuterodimethylsulfoxide using tetramethylsilane as reference is described in Table 5.

Table 5.

| Chemical Shift δ(ppm) | Relative Area | NMR Characteristics Example 8 Structural Feature | Multiplicity |
|---|---|---|---|
| 8.32 | 1 | indoline H-7 | doublet of doublets |
| 5.75 | 1 | indoline H-2 | doublet of doublets (J=3.5 and 10.0 cps) |
| 10.98 | 1 | indole NH | broad singlet |
| 1.14 | 3 | pyrroline $CH_3$-5 | doublet |

Table 5.-continued

| Chemical Shift δ(ppm) | Relative Area | NMR Characteristics Example 8 Structural Feature | Multiplicity |
|---|---|---|---|
| 1.7–4.0 | 7 | indoline H-3 and pyrroline H-3, H-4, and H-5 | (J=6.2 cps) broad singlet |

EXAMPLE 9.

2,3,5,6-Tetrahydro-5-(indol-3-yl)-3,3-dimethyl-1H-pyrrolinyl[2,1-b][1,3]benzodiazepine.

A solution of 8.5 g. of 1-[2-(5,5-dimethyl-1-pyrrolinyl)]-2-(3-indolyl)indoline (Example 11) in 250 ml. of n-butanol is refluxed for 63 hrs. The progress of the reaction is assayed during this period by thin layer chromatography on a glass plate coated with alumina. Small aliquots of the reaction mixture are removed at intervals, the solvent evaporated and the residue dissolved in a small amount of chloroform containing 10% ethanol. This is used to prepare the thin layer chromatogram. For comparison a parallel chromatogram is made on the same plate from the starting material. Iodine serves as indicator after exposure of the developed plates to an atmosphere of iodine in a closed chamber. After 65 hrs. the presence of the product is evident from a rather strong spot which develops at Rf 2.3 as compared to the faster moving starting material which appears at Rf 8.2. The product can be detected by thin layer chromatography early in the reaction period, at 15 hrs., but even after 63 hrs. some of the starting material remains. The reaction is, nevertheless, terminated and the solvent removed by vacuum evaporation. The residue is triturated with 100 ml. of hot acetone and filtered from insoluble material weighing 2.2 g. On chilling the filtrate a further 2.1 g. of material is obtained. Both portions of acetone insoluble material can be identified as desired product contaminated with unreacted indoline starting material by examination of the infrared spectra. Absorption at 13.5μ is characteristic of the benzodiazepine compound, and differences in the depths of the maxima in the 6.20 to 6.41μ region are also useful empirical guides for distinguishing indoline and diazepine compounds. The intensities of these two peaks are reversed for these two isomeric structures, the shorter wave length showing the stronger absorption for the benzodiazepine. The foregoing samples are combined, 4.3 g. in aggregate, dissolved in 250 ml. of boiling absolute ethanol, and the desired product recovered after crystallization, yield 3.4 g., m.p. 212.5°–213.5° C.

Anal. Calcd. for $C_{22}H_{23}N_2$: C, 80.21; H, 7.04; N, 12.75. Found: C, 80.20; H, 7.04; N, 12.78.

The nuclear magnetic resonance spectrum measured in deuterodimethylsulfoxide using tetramethylsilane as reference has the following characteristics:

Table 6.

| Chemical Shift δ(ppm) | Relative Area | NMR Characteristics Example 9 Multiplicity | Structural Feature |
|---|---|---|---|
| 7.71 | 1 | doublet of doublets | 10-position |
| 10.48 | 1 | broad singlet | indole NH |
| 5.38 | 1 | doublet of doublets | 5-position |
| 2.1–3.5 | 4 | broad singlet | 1 and 6-positions |

Table 6.-continued

NMR Characteristics Example 9

| Chemical Shift δ(ppm) | Relative Area | Multiplicity | Structural Feature |
|---|---|---|---|
| 1.02 | 3 | singlet | 3-CH₃ |
| 1.31 | 3 | singlet | 3-CH₃ |
| 1.88 | 2 | multiplet | 2-position |

EXAMPLES 10-25 Additional 2-(3-Indolyl)-1-substituted-indolines.

The products which are listed in Table 7 are prepared by adaptation of the methods of Examples 1 or 3 through substitution of various other carboxamide starting materials for 2-pyrrolidone on a molecular equivalent basis. One molecular proportion of triethylamine is included in the reaction mixtures of these additional preparations to serve as a neutralizing agent for evolved hydrogen chloride. None of the substances shown in Table 7 is prone to rearrangement on warming in ethanol to a pyrrolobenzodiazepine. The hydrochloride salts are prepared from these products according to the method of Example 4. Table 7 contains a tabulation of the various carboxamide reactants, the products, and physical properties of the products. In each instance the structure of the product is confirmed by examination of the infrared absorption and nuclear magnetic resonance spectra. With respect to the latter, the chemical shifts for the H-2 and H-7 indoline protons, with the coupling constants for the former, are given. They illustrate the values characteristically exhibited for these key features in structure illucidation. Application of the method to various ring substituted indole dimers is illustrated in Examples 20-25. The substituted indolylindolines required as starting materials for Examples 20-25 are prepared by dimerization of the correspondingly substituted indole according to the following procedure.

Preparation of 5-bromo-2-(5-bromo-3-indolyl)indoline.

A solution of 5-bromoindole (9.8 g., 0.05 mole) in 250 ml. of dry benzene is cooled in an ice water bath while dry hydrogen chloride gas is admitted at a brisk rate for a period of 1 hr. The mixture is kept in the ice water bath for 1 additional hour and the product in the form of the hydrochloride salt then collected by filtration, weight 8.5 g., m.p. 158°-160° C. (dec.). This material is converted to the base by agitation with a mixture of 200 ml. of ether in 10 ml. of concentrated ammonium hydroxide. The ether layer is separated, washed and concentrated to yield the base as an oil which commences to crystallize. It is recrystallized from heptene-benzene to yield 6.1 g. (62%). The following intermediates are prepared in similar fashion.

5-nitro-2-(5-nitro-3-indolyl)indoline, m.p. 200°-202° C.; recrystallized ethanol, yield 44%

5-cyano-2-(5-cyano-3-indolyl)indoline, m.p. 214°-216° C.; recrystallized ethanol, yield 40%

5-methoxy-2-(5-methoxy-3-indolyl)-indoline, m.p. 140°-141° C.; recrystallized ethanol-benzene, yield 87%

5-benzyloxy-2-(5-benzyloxy-3-indolyl)-indoline, m.p. 103°-105° C.; recrystallized benzene, yield 74%.

Table 7

Products of Examples 10-25, Formula I

| EX. NO. | REACTANT | PRODUCT | m.p. (° C.) | RECRYSTALLIZATION SOLVENTS | ANALYSIS Calcd. Found | | H-2 AND H-7 NMR CHEMICAL SHIFTS (ppm) | | |
|---|---|---|---|---|---|---|---|---|---|
| | | | | | | | H-2 | H-7 | Solvent |
| 10 | N-Methylformamide | 2-(3-Indolyl)-1-[methylimino)methyl]-indoline Hydrochloride | 213.5-214.5 | ethanol-ether | C 69.33 H 5.82 N 13.48 | 69.29 6.03 13.44 | 5.77(J= 5.0 and 9.2 cps) | not observed | CHCl₃ |
| 11 | 5,5-Dimethyl-2-pyrrolidinone | 1-[2-(5,5-Dimethyl-1-pyrrolinyl)]-2-(3-indolyl)indoline Hydrochloride | 260-261 | ethanol-ether | C 72.22 H 6.61 N 11.48 | 72.33 6.60 11.41 | 5.73(J= 3.0, 10.0 cps) | 8.27 | (CD₃)₂SO |
| 12 | N-(tert-Butyl)-formamide | 1-[(tert-Butylimino)-methyl]-2-(3-indolyl)-indoline Hydrochloride | 233.5-234.5 | ethanol | C 71.27 H 6.84 N 11.87 | 71.57 7.01 11.75 | 5.71(J= 5.4, 9.6 cps) | 7.71 | CDCl₃ |
| 13 | N-Ethylformamide | 1-[(Ethylimino)methyl]-2-(3-indolyl)indoline Hydrochloride | 215.5-216.5 | ethanol-ether | C 70.03 H 6.19 N 12.90 | 69.77 6.03 12.79 | 5.74(J= 5.2, 9.6 cps) | 7.57 | CDCl₃ |
| 14 | N-Cyclohexylformamide | 1-(Cyclohexyliminomethyl)-2-(3-indolyl)-indoline Hydrochloride | 201.5-203.5 | ethanol-ether | C 72.71 H 6.90 N 11.06 | 72.94 6.80 11.11 | 5.75(J= 5.5, 9.7 cps) | 7.68 | CDCl₃ |
| 15 | N-Isopropyl-formamide | 2-(3-Indolyl)-1-[isopropylimino)methyl]-indoline Hydrochloride | 215.5-217.5 | ethanol-ether | C 70.68 H 6.53 N 12.36 | 70.92 6.69 12.29 | 5.65(J= 5.3, 10.0 cps) | 7.65 | CDCl₃ |
| 16 | N-Cyclopentyl-formamide | 1-(Cyclopentyliminomethyl)-2-(3-indolyl)-indoline Hydrochloride | 215.5-217.5 | ethanol | C 72.21 H 6.61 N 11.49 | 72.02 6.74 11.22 | 5.66(J= 5.5, 9.5 cps) | 7.07 | CDCl₃ |
| 17 | N-Cycloheptyl-formamide | 1-(Cycloheptyliminomethyl)-2-(3-indolyl)-indoline Hydrochloride | 182.5-184.5 | ethanol | C 73.17 H 7.16 N 10.67 | 73.00 7.13 10.67 | 5.72(J= 5.4, 9.5 cps) | 7.61 | CDCl₃ |
| 18 | N-Cyclooctyl-formamide | 1-(Cyclooctyliminomethyl)-2-(3-indolyl)-indoline Hydrochloride Hemihydrate | 214-216.5 | ethanol-ether | C 72.01 H 7.49 N 10.08 | 72.22 7.43 9.98 | not observed | 7.67 | CDCl₃ |
| 19 | N-(1-Admantyl)-formamide | 1-[(1-Admantylimino)-methyl]-2-(3-indolyl)-indoline Hydrochloride | 230.5-232.5 | ethanol-ether | C 75.06 H 7.00 N 9.73 | 74.96 7.06 9.59 | 5.99 (multiplet) | not observed | CF₃CO₂H |
| 20 | N-Isopropyl-formamide; and 5-bromo-2-(5-bromoindol-3-yl)-indoline | 5-Bromo-2-(5-bromo-3-indolyl)-1-[(isopropylimino)methyl]indoline Hydrochloride Hemiethanolate | 189.5-191.5 | ethanol-ether | C 48.44 H 4.45 N 8.07 | 47.90 4.45 8.23 | 6.39(J= 3.0, 9.0 cps) | not observed | (CD₃)₂SO |
| 21 | 2-Pyrrolidone; and 5-nitro-2-(5-nitroindol-5-yl)indoline | 5-Nitro-2-(5-Nitro-3-indolyl)-1-[2-(1-pyrrolinyl)]indoline | 234.5-237.5 | ethanol-heptane | C 56.15 H 4.24 N 16.37 | 56.06 4.23 16.18 | | | |

Table 7-continued

| | | | Products of Examples 10–25, Formula I | | | | H-2 AND H-7 NMR CHEMICAL SHIFTS (ppm) | | |
|---|---|---|---|---|---|---|---|---|---|
| EX. NO. | REACTANT | PRODUCT | m.p. (° C.) | RECRYSTALLIZA- TION SOLVENTS | ANALYSIS Calcd. | Found | H-2 | H-7 | Solvent |
| 22 | 3-yl)indoline N-Isopropyl- formamide; and 5-benzyloxy-2- (5-benzyloxyin- dol-3-yl)indol- ine | Hydrochloride 5-Benzyloxy-2-(5- benzyloxy-3-indolyl)- 1-[(isopropylimino)- methyl]indoline Hy- drochloride | 222–223 | ethanol | C 73.96 H 6.21 N 7.61 | 73.90 6.05 7.71 | | | |
| 23 | N-Isopropyl- formamide; and 5-nitro-2-(5- nitroindol-3- yl)indoline | 1-[(Isopropylimino)- methyl]-5-nitro-2- [3-(5-nitroindolyl)]- indoline | 215.5–216.5 | ethanol- acetone | C 61.06 H 4.87 N 17.80 | 61.22 4.87 17.51 | 6.01(J= 4.6, 10.2 cps) | 7.80 | (CD$_3$)$_2$SO |
| 24 | N-Isopropyl- formamide; and 5-cyano-2-(5- cyanoindol-3- yl)indoline | 5-Cyano-2-(5-cyano- 3-indolyl)-1-[(iso- propylimino)methyl]- indoline | 223.5–225.5 | ethanol- chloroform | C 74.76 H 5.42 N 19.82 | 75.20 5.44 19.79 | 5.84(J= 5.0, 10.0 cps) | 7.85 | (CD$_3$)$_2$SO |
| 25 | N-Isopropylfor- mamide; and 5- methoxy-2-(5- methoxyindol-3- yl)indoline | 1-[(Isopropylimino)- methyl]-5-methoxy-2- (5-methoxy-3-indolyl)- indoline Hydrochloride | 204.5–206.5 | ethanol | C 66.07 H 6.55 N 10.51 | 65.43 6.61 10.31 | 6.40(J= 3.0, 7.5 cps) | 7.79 | (CD$_3$)$_2$SO |

EXAMPLE 26.

3-Methyl-2-(3-methylindol-2-yl)-1-[2-(1-pyrrolinyl)-]indoline hydrochloride.

The following materials are used:
3-Methyl-2-(3-methylindol-2-yl)indoline, 10.5 g. (0.04 mole)
2-Pyrrolidinone, 3.4 g. (0.04 mole)
Triethylamine, 4.05 g. (0.04 mole)
Phosphorus oxychloride, 6.14 g. (0.04 mole)
1,2-Dichloroethane, 150 ml.

The foregoing materials, except for the phosphorus oxychloride are dissolved in 125 ml. of the 1,2-dichloroethane and the mixture is cooled to −20° C. in a dry ice bath. The phosphorus oxychloride is dissolved in the remainder of the 1,2-dichloroethane and added in dropwise fashion to the other materials during a period of 45 minutes while maintaining the temperature of the mixture at about −20° C. The mixture is stirred during the entire period. The cooling bath is then removed and the mixture is allowed to warm to room temperature with stirring during 2½ hrs. The product is then recovered by pouring the reaction mixture into a solution of 35 g. of sodium acetate in 100 ml. of water (or a similar volume of conc. aq. NH$_4$OH, 29%) containing ice. The reaction is adjusted to pH 14 with potassium hydroxide when sodium acetate solution is used above, and the product which precipitates is recovered by filtration, 9.78 g. (74%) m.p. 253°–254° C. (dec.).

The foregoing material is then converted to the hydrochloride salt by suspending 8.78 g. thereof in 200 ml. of ethanol containing 7 ml. of 5.3 N ethanolic hydrogen chloride. The suspension is heated on a steam bath until the hydrochloride salt forms and dissolves. The hot solution is filtered and then mixed with 200 ml. of ether. The hydrochloride salt precipitates and is collected on a filter. It is recrystallized from 200 ml. of ethanol mixed with 200 ml. of ether and finally from 175 ml. of ethanol, yield 3.44 g. The melting point and elemental analysis of this material is reported in Table 8.

Table 8 also contains a listing of analogous skatole dimer derivatives of Formula II which may be prepared according to Example 26 from other carboxamide reactants substituted for 2-pyrrolidinone. It no instance is rearrangement of any of these substances to a pyrrolobenzodiazepine found to occur. The indoline structure is confirmed by the downfield shift of the indoline H-7 nmr resonance similar to that observed in the nmr spectra of the Formula I indolylindolines listed in Table 7. Due to the presence of the 3-methyl substituent in the indoline ring of the compounds of Formula II, the chemical shift for the H-2 resonance of the substances is not instrumental in structure identification. The H-7 chemical shift of the nmr spectra, the elemental analyses, and physical properties, for these compounds are also given in Table 8. In each instance the H-7 shift is a doublet of doublets equivalent in intensity to one proton on integration.

TABLE 8

| | | Products of Examples 26–38, Formula II | | | | | |
|---|---|---|---|---|---|---|---|
| EX. NO. | REACTANT | PRODUCT | m.p.(° C.) | RECRYSTALLIZA- TION SOLVENT | ANALYSIS Calcd. | Found | H-7 NMR CHEMICAL SHIFT, δ (ppm) |
| 26 | 2-Pyrrolidi- none | 3-Methyl-2-(3-methyl- indol-2-yl)-1-[2-(1- pyrrolinyl)]indoline | 261.5–263.5 | ethanol | C 72.21 H 6.61 N 11.49 | 71.97 6.61 11.25 | 8.3 |
| 27 | N-Methylform- amide | 3-Methyl-1-[(methyl- imino)methyl]-2-(3- methylindol-2-yl)- indoline Hydrochloride | 229.5–230.5 | ethanol- ether | C 70.68 H 6.53 N 12.36 | 70.38 6.34 12.20 | 7.68 |
| 28 | N-Methylacet- amide | 3-Methyl-1-[1-(methyl- imino)ethyl]-2-(3- methylindol-2-yl)- indoline Hydrochlor- ide | 203.5–206.5 | ethanol | C 71.27 H 6.84 N 11.87 | 71.28 6.82 11.78 | 8.09 |

TABLE 8-continued

Products of Examples 26-38, Formula II

| EX. NO. | REACTANT | PRODUCT | m.p.(° C.) | RECRYSTALLIZATION SOLVENT | ANALYSIS Calcd. Found | | H-7 NMR CHEMICAL SHIFT, δ (ppm) |
|---|---|---|---|---|---|---|---|
| 29 | ε-Caprolactam | 1-[7-(3,4,5,6-Tetrahydro-2H-azepinyl)]-3-methyl-2-(3-methylindol-2-yl)indoline Hydrochloride Hemiethanolate | 182.5–184.5 | ethanol-ether | C 72.00 H 7.50 N 10.08 | 71.77 7.49 9.88 | 7.81 |
| 30 | 5,5-Dimethyl-2-pyrrolidinone | 1-[2-(5,5-Dimethyl-1-pyrrolinyl)]-3-methyl-2-(3-methylindol-2-yl)indoline Hydrochloride | 225.5–227.5 | ethanol-ether | C 73.17 H 7.16 N 10.66 | 73.06 7.25 10.49 | 8.22 |
| 31* | 5-Methyl-2-Pyrrolidinone | 3-methyl-2-(3-methylindol-2-yl)-1-[2-(5-methyl-1-pyrrolinyl)]indoline Hydrochloride ¼ Hydrate, Isomer A | 202–204 | ethanol-ether | C 71.86 H 6.95 N 10.93 | 71.90 7.07 10.75 | 8.32 |
| 32* | 5-Methyl-2-pyrrolidinone | 3-Methyl-2-(3-methylindol-2-yl)-1-[2-(5-methyl-1-pyrrolinyl)]indoline, Hydrochloride Isomer B | 234–236.5 | ethanol ether | C 72.71 H 6.90 N 11.06 | 72.67 7.01 10.99 | 8.31 |
| 33 | N-Cyclopentylformamide | 1-[(Cyclopentylimino)-methyl]-3-methyl-2-(3-methylindol-2-yl)indoline Hydrochloride | 200–201 | ethanol-ether | C 73.17 H 7.16 N 10.67 | 73.56 7.23 10.71 | 7.55 |
| 34 | N-Cyclohexylformamide | 1-[(Cyclohexylimino)-methyl]-3-methyl-2-(3-methylindol-2-yl)-indoline Hydrochloride | 211.5–213.5 | ethanol ether | C 73.60 H 7.41 N 10.30 | 73.66 7.38 10.24 | 7.65 |
| 35 | N-Isopropylformamide | 1-[(Isopropylimino) methyl]-3-methyl-2-(3-methylindol-2-yl)-indoline Hydrochloride | 208.5–210.5 | ethanol ether | C 71.81 H 7.13 N 11.42 | 72.10 7.03 11.54 | 8.02 |
| 36 | N-(tert-Butyl)-formamide | 1-[(tert-Butylimino) methyl]-3-methyl-2-(3-methylindol-2-yl)indoline Hydrochloride | 226.5–228.5 | ethanol-ether | C 72.33 H 7.39 N 11.00 | 72.36 7.41 11.01 | 7.63 |
| 37 | N-Cycloheptylformamide | 1-[(Cycloheptylimino) methyl]-3-methyl-2-(3-methylindol-2-yl) indoline Hydrochloride | 211.5–213.5 | ethanol-ether | C 74.00 H 7.64 N 9.96 | 73.82 7.69 9.88 | not examined |
| 38 | N-Cyclooctylformamide | 1-[(Cyclooctylimino) methyl]-3-methyl-2-(3-methylindol-2-yl)indoline Hydrochloride | 206–207 | ethanol-ether | C 74.37 H 7.86 N 9.64 | 74.59 7.56 9.46 | 7.58 |

*The products of Examples 31 and 32 are isomeric racemates derived from the same experimental preparation. The product of Example 31 is referred to as isomer A. Isomer A was recovered by filtration after quenching the 1,2-dichloroethane reaction mixture in concentrated aqueous ammonium hydroxide as specified in Example 26. Isomer A was recrystallized from ethanol and then converted to the hydrochloride salt by treatment with ethanolic hydrogen chloride as described in Example 26. The product of Example 32 is referred to as isomer B. It was recovered by separating and concentrating the dichloroethane solvent layer after quenching the reaction mixture with aqueous ammonium hydroxide as described in Example 26. Isomer B was first purified by recrystallization from ethanol and then converted to the hydrochloride salt in the fashion described for Example 26.

EXAMPLE 39. Resolution of 2,3,5,6-tetrahydro-5-(indol-3-yl)-1H-pyrrolo[2,1-b][1,3]benzodiazepine into the pure d and l-isomers.

An ethanolic solution of the product of Example 3 is treated with an equivalent amount of D-(l)-di-p-toluoyltartaric acid. l-2,3,5,6-Tetrahydro-5-(indol-3-yl)-1H-pyrrolo-[2,1-b][1,3]benzodiazepine D-(l)-di-p-toluoyltartrate, being less soluble, crystallizes. Repeated recrystallization from ethanol yields the pure salt, m.p. 176.5° C. (dec.) and $[\alpha]_D^{25} = -118.6$ (C = 1%, methanol). The filtrates are combined, basified with concentrated aqueous ammonium hydroxide, and concentrated to recover crude free base enriched in d-form. Treatment thereof with L-(d)-di-p-toluoyltartaric acid in ethanolic solution yields pure d-2,3,5,6-tetrahydro-5-(indol-3-yl)-1H-pyrrolo-[2,1-b][1,3]benzodiazepine L-(d)-di-p-toluoyltartrate, m.p. 174°–175° C. (dec.), $[\alpha]_D^{25} = +119.5$ (C = 1%, methanol). The foregoing salts are converted to the corresponding hydrochloride salts by treatment with ethanolic HCl in ethanol. The d and l forms of 2,3,5,6-tetrahydro-5-(indol-3-yl)-1H-pyrrolo[2,1-b][1,3]benzodiazepine hydrochloride have the following physical properties.

| | | M.P. (Corr.). | $[\alpha]_D^{25}$ (C = 1%, methanol) |
|---|---|---|---|
| d - | form | 251.5–253.5° | + 81.0 |
| l - | form | 252.5–254.5° | − 80.2 |
| d,l - | form | 262–264° | 0 |

What is claimed is:

1. The process of exerting a therapeutic effect selected from the group consisting of diuretic, antithrombogenic, and antiarrhythmic in a mammal in need thereof which comprises administering thereto a nontoxic oral or parenteral dose effective to exert diuretic, antithrombogenic, or antiarrhythmic action of from 0.1 to 25 mg./kg. of body weight of a compound selected from the group consisting of the bases having the formulas

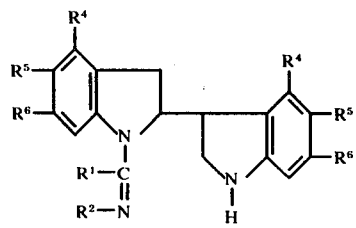

Formula I

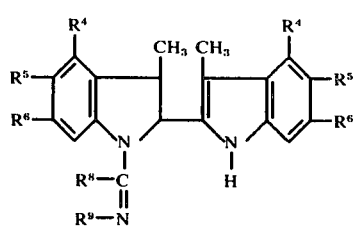

Formula II

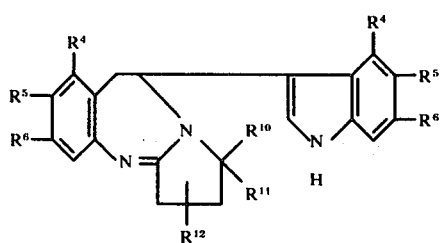

Formula III and a pharmaceutically acceptable acid addition salt of said bases
wherein

- $R^1$ and $R^8$ are hydrogen or lower alkyl having from 1 to 4 carbon atoms,
- $R^2$ and $R^9$ are alkyl having from 1 to 8 carbon atoms, cycloalkyl, or polycycloalkyl having from 3 to 10 carbon atoms, or
- $R^1$ and $R^2$ are joined to form a 2-(1-pyrrolinyl) group which is unsubstituted or carbon substituted by up to 3 alkyl groups each having from 1 to 4 carbon atoms, or
- $R^8$ and $R^9$ are joined to form a 5, 6, or 7-membered heterocyclic ring which is unsubstituted or carbon substituted by up to 3 alkyl groups each having from 1 to 4 carbon atoms,
- $R^4$, $R^5$, and $R^6$ are hydrogen, halogen, alkyl having 1 to 4 carbon atoms, alkoxy having 1 to 12 carbon atoms, aralkoxy having 7 to 12 carbon atoms, alkanoyl having 2 to 4 carbon atoms, nitro, or cyano, and
- $R^{10}$, $R^{11}$, and $R^{12}$ are hydrogen or lower alkyl having from 1 to 4 carbon atoms and $R^{12}$ is located in either the 1- or 2-positions.

2. The process of claim 1 wherein 2-(3-indolyl)-1-[2-(1-pyrrolinyl)]indoline or a pharmaceutically acceptable acid addition salt thereof is employed.

3. The process of claim 1 wherein 2-(3-indolyl)-1-[2-(5-methyl-1-pyrrolinyl)]indoline or a pharmaceutically acceptable acid addition salt thereof is employed.

4. The process of claim 1 wherein 1-[tert.-butyliminomethyl]-2-(3-indolyl)indoline or a pharmaceutically acceptable acid addition salt thereof is employed.

5. The process of claim 1 wherein 1-[ethyliminomethyl]-2-(3-indolyl)indoline or a pharmaceutically acceptable acid addition salt thereof is employed.

6. The process of claim 1 wherein 2-(3-indolyl)-1-[isopropyliminomethyl]indoline or a pharmaceutically acceptable acid addition salt thereof is employed.

7. The process of claim 1 wherein 1-(cyclopentyliminomethyl)-2-(3-indolyl)indoline or a pharmaceutically acceptable acid addition salt thereof is employed.

8. The process of claim 1 wherein 1-(isopropyliminomethyl)-5-methoxy-2-(5-methoxy-3-indolyl)indoline or a pharmaceutically acceptable acid addition salt thereof is employed.

9. The process of Claim 1 wherein 3-methyl-1-[1-(methylimino)-ethyl]-2-(3-methylindol-2-yl)indoline or a pharmaceutically acceptable acid addition salt thereof is employed.

10. The process of claim 1 wherein 1-[2-(5,5-dimethyl-1-pyrrolinyl)]-3-methyl-2-(3-methylindol-2-yl)indoline or a pharmaceutically acceptable acid addition salt thereof is employed.

11. The process of claim 1 wherein 3-methyl-2-(3-methylindol-2-yl)-1-[2-(1-pyrrolinyl)]indoline or a pharmaceutically acceptable acid addition salt thereof is employed.

12. The process of claim 1 wherein 3-methyl-1-[(methylimino)methyl]-2-(3-methylindol-2-yl)indoline or a pharmaceutically acceptable acid addition salt thereof is employed.

13. The process of claim 1 wherein 1-[7-(3,4,5,6-tetrahydro2H-azepinyl)]-3-methyl-2-(3-methylindol-2-yl)indoline or a pharmaceutically acceptable acid addition salt thereof is employed.

14. The process of claim 1 wherein 3-methyl-2-(3-methylindol-2-yl)-1-[2-(5-methyl-1-pyrrolinyl)]indoline or a pharmaceutically acceptable acid addition salt thereof is employed.

15. The process of claim 1 wherein 1-[(cyclopentylimino)-methyl]-3-methyl-2-(3-methylindol-2-yl)indoline or a pharmaceutically acceptable acid addition salt thereof is employed.

16. The process of claim 1 wherein 1-[(cyclohexylimino)methyl]-3-methyl-2-(3-methylindol-2-yl)indoline or a pharmaceutically acceptable acid addition salt thereof is employed.

17. The process of claim 1 wherein 1-[(isopropylimino)-methyl]-3-methyl-2-(3-methylindol-2-yl)indoline or a pharmaceutically acceptable acid addition salt thereof is employed.

18. The process of claim 1 wherein 1-[(tert.-butylimino)-methyl]-3-methyl-2-(3-methylindol-2-yl)indoline or a pharmaceutically acceptable acid addition salt thereof is employed.

19. The process of claim 1 wherein 1-[(cycloheptylimino)methyl]-3-methyl-2-(3-methylindol-2-yl)indoline or a pharmaceutically acceptable acid addition salt thereof is employed.

20. The process of claim 1 wherein 1-[(cyclooctylimino)-methyl]-3-methyl-2-(3-methylindol-2-yl)indoline or a pharmaceutically acceptable acid addition salt thereof is employed.

21. The process of claim 1 wherein 2,3,5,6tetrahydro-5-(indol-3-yl)-1H-pyrrolo[2,1-b][1,3]benzodiazepine or a pharmaceutically acceptable acid addition salt thereof is employed.

22. The process of claim 1 wherein 2,3,5,6-tetrahydro-5-(indol-3-yl)-3,3-dimethyl-1H-pyrrolo[2,1-b][1,3]benzodiazepine or a pharmaceutically acceptable acid addition salt thereof is employed.

23. The process of claim 1 wherein 2,3,5,6-tetrahydro-5-(indol-3-yl)-3-methyl-1H-pyrrolo[2,1-b][1,3]benzodiazepine or a pharmaceutically acceptable acid addition salt thereof is employed.

* * * * *